United States Patent
Keatch

(10) Patent No.: US 9,188,511 B2
(45) Date of Patent: Nov. 17, 2015

(54) SAMPLING DEVICE FOR OILFIELD APPLICATIONS

(76) Inventor: Richard Keatch, Coull (GB)

(*) Notice: Subject to any disclaimer, the term of this patent is extended or adjusted under 35 U.S.C. 154(b) by 937 days.

(21) Appl. No.: 13/266,155

(22) PCT Filed: Apr. 27, 2010

(86) PCT No.: PCT/US2010/032588
§ 371 (c)(1),
(2), (4) Date: Feb. 14, 2012

(87) PCT Pub. No.: WO2010/129286
PCT Pub. Date: Nov. 11, 2010

(65) Prior Publication Data
US 2012/0134140 A1    May 31, 2012

Related U.S. Application Data

(60) Provisional application No. 61/173,047, filed on Apr. 27, 2009.

(51) Int. Cl.
*G01N 1/00* (2006.01)
*G01N 1/08* (2006.01)
*G01N 1/10* (2006.01)

(52) U.S. Cl.
CPC .......... *G01N 1/08* (2013.01); *G01N 2001/1025* (2013.01)

(58) Field of Classification Search
CPC ............. G01N 1/26; G01N 1/00; G01N 1/20; G01N 1/02; G01N 1/12
USPC .......................................................... 73/863
See application file for complete search history.

(56) References Cited

U.S. PATENT DOCUMENTS

| | | | |
|---|---|---|---|
| 3,967,393 A | 7/1976 | Nixon | |
| 4,336,709 A | 6/1982 | Meek | |
| 2006/0000278 A1 | 1/2006 | Reeves | |
| 2008/0121050 A1* | 5/2008 | Sakal et al. | 73/863.21 |

FOREIGN PATENT DOCUMENTS

| | | |
|---|---|---|
| EP | 1464944 A1 | 10/2004 |
| JP | 05-256082 A | 10/1993 |

OTHER PUBLICATIONS

Examination Report issued in corresponding British Application No. GB1120539.0; Dated May 10, 2013 (2 pages).
International Search Report issued in PCT/US2010/032588, mailed on Feb. 1, 2011, 2 pages.
Written Opinion issued in PCT/US2010/032588, mailed on Feb. 1, 2011, 4 pages.
Examination Report issued in corresponding British Application No. GB1120539.0; Dated Oct. 1, 2013 (1 page).

* cited by examiner

*Primary Examiner* — Hezron E Williams
*Assistant Examiner* — Rodney T Frank
(74) *Attorney, Agent, or Firm* — Osha Liang LLP

(57) ABSTRACT

A sample collecting device including an outer casing and a valve assembly disposed at least partially within the outer casing and configured to obtain a sample of a sample material. A method of sampling sediment including entering a sample collecting device into a fluid storage container, contacting a surface of a sample material with the sample collecting device, obtaining a sample of the sample material, and removing the sample collecting device from the fluid storage container.

21 Claims, 5 Drawing Sheets

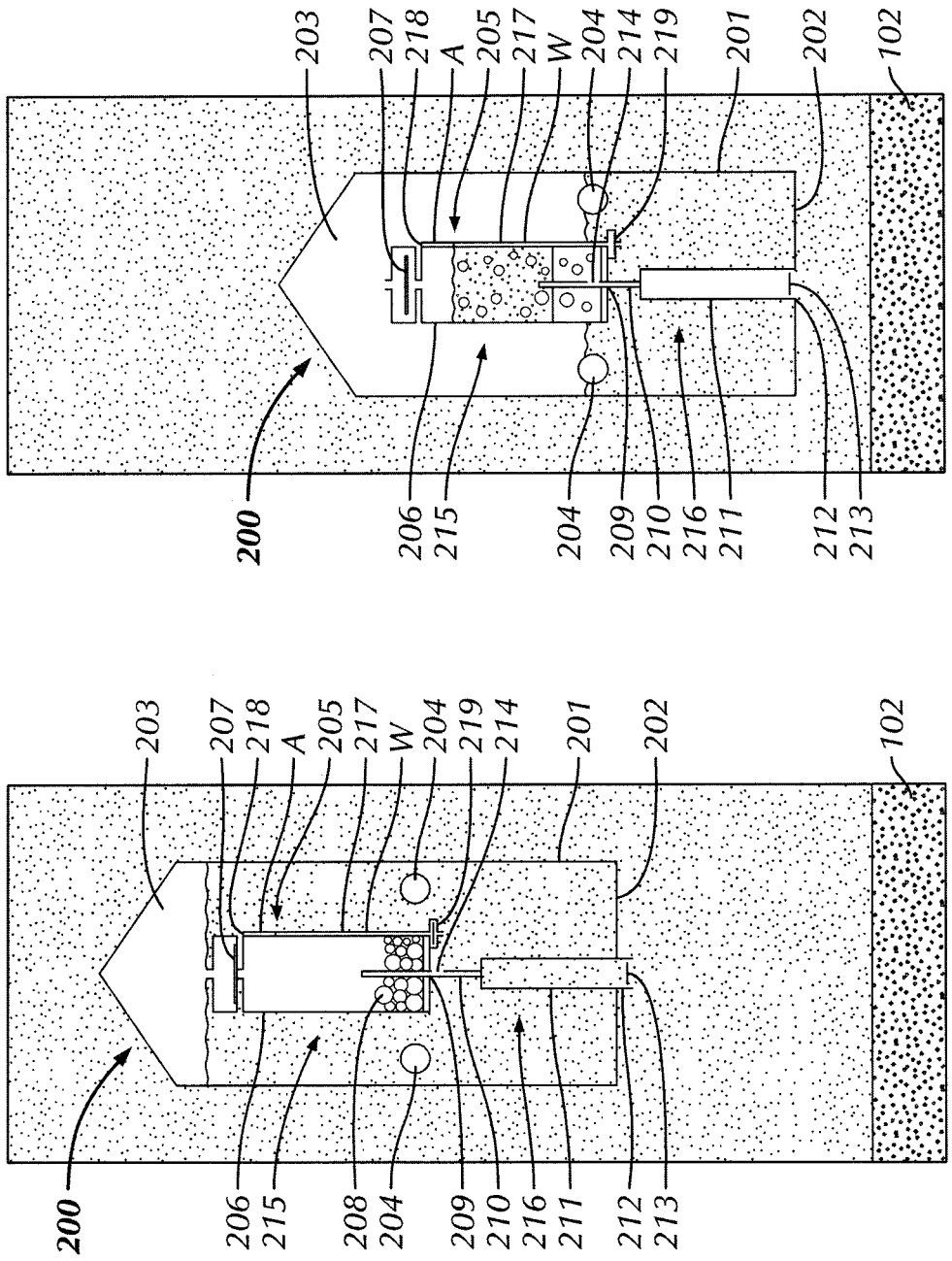

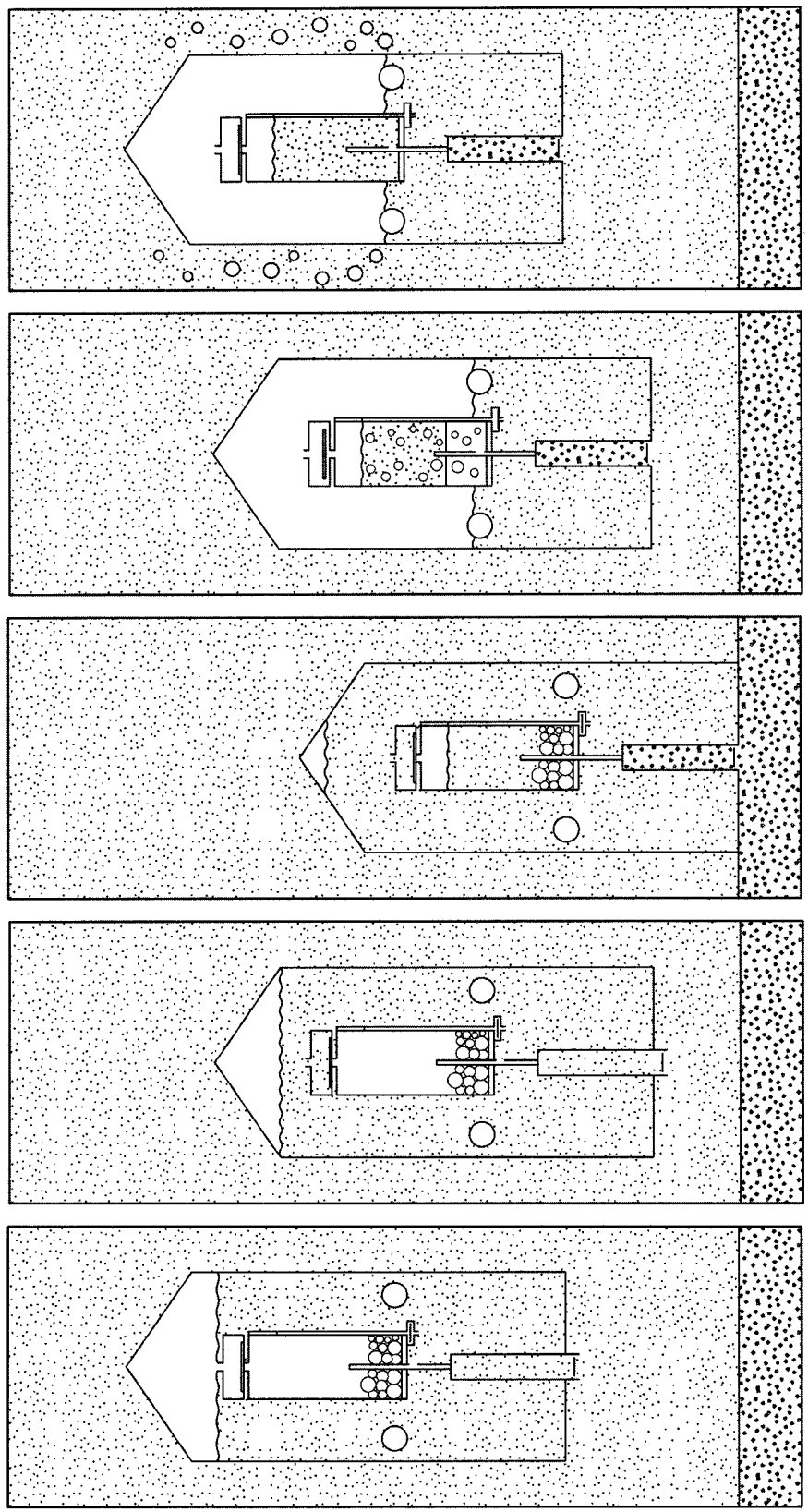

SAMPLING DEVICE FOR OILFIELD APPLICATIONS

BACKGROUND OF INVENTION

1. Field of the Invention

Embodiments disclosed here generally relate to obtaining a sample. More particularly, the present disclosure relates to apparatus and methods to obtain a sample of sediment from the bottom of a produced fluid storage container.

2. Background Art

Many oilfield installations located off-shore, particularly in the North Sea, use produced fluid storage containers made of concrete that are located on the sea bed. The storage containers are designed to contain fluids produced from wells drilled deep into a reservoir and to allow separation of crude oil from co-produced connate water. Typically, there are many large storage containers for each offshore installation; each container may be around ten meters in diameter and over fifty meters deep.

The produced fluid is pumped into the storage container through an import/export pipe located near the top of the storage container. The produced oil has a lower density than the produced connate water and, thus, separates and forms a layer on top of the water within the storage container. Once separated, the oil in the storage containers may be exported from the storage container via the import/export pipe located near the top of the storage container. There is a dead volume between the export pipe and the top of the storage container that may be occupied by crude oil and gasses. As the oil is removed from the produced fluid storage container, its volume is replaced by seawater which enters via a pipe located near the bottom of the storage container. The seawater may be stored in a header tank which maintains a hydrostatic pressure of several bars depending on the design of the storage containers.

When the production of oil from the reservoir is no longer viable, there is a need to decommission the platform and clean up the storage containers. To remove all oil from the storage container, the process of displacing oil with seawater continues until only the dead volume of hydrocarbon gasses and seawater remain. To remove the hydrocarbon gasses, a gas lighter than the hydrocarbon gas, preferably carbon dioxide, is introduced into the storage container to displace the hydrocarbon gas. Only the displacement gas and seawater remain in the storage container after the hydrocarbon gas is removed through the export pipe. Finally, the contents of the storage container are treated with a chemical solution to absorb the displacement gas and to convert the remaining contents of the storage container into briny water. However, in most cases, the storage container further contains sediment which prevents safe disposal of the container.

Sediment build-up occurs over many years of production operation. A variety of solid wastes can be introduced into or form within the storage containers resulting in the development of a layer of sediment. For example, the mixing of incompatible brines, such as produced connate water and seawater, can result in the precipitation of mineral scales, such as barium sulphate or calcium carbonate to the bottom of the storage container, and naphthenic acids present in the crude oil can react with calcium-rich brine to form calcium naphthenate deposits. Sand and mud may also be produced which settle to the bottom of the storage container. The accumulated sediment may require special handling and disposal methods due to hydrocarbon materials and naturally occurring radioactive minerals that may be entrained therein. Naturally occurring radioactive minerals such as radium-226 sulphate, lead-210 metal, and a series of other radioisotopes resulting from the decay of uranium and thorium may be present in the water contained within the pores of reservoir rock. A sample must be obtained to determine the composition of the sediment in order to determine the proper method for removal or treatment of the storage container.

The only access to the inside of the storage container is typically through the import and export pipes that have an inner diameter typically around 10-12 inches and follow convoluted paths often containing several 90 degree bends. Furthermore, the storage containers lie in deep water such that the top of the containers may be more than 100 meters below the surface of the sea, thus rendering problematic the option of drilling into the container to retrieve a sample.

Accordingly, there exists a need for a sampling device capable of passing through sharp bends in the import and export pipes leading to and from a produced fluid storage container located on a sea floor. Furthermore, there exists a need for a sampling device designed to locate sediment, measure the depth of the sediment, collect a sample, and return to a desired altitude within the container for retrieval without operator input.

SUMMARY OF INVENTION

In one aspect, embodiments disclosed herein relate to a sample collecting device including an outer casing, and a valve assembly disposed at least partially within the outer casing and configured to obtain a sample of a sample material.

In another aspect, embodiments disclosed herein relate to a method of sampling sediment, the method including entering a sample collecting device into a fluid storage container, contacting a surface of a sample material with the sample collecting device, obtaining a sample of the sample material, and removing the sample collecting device from the fluid storage container.

Other aspects and advantages of the invention will be apparent from the following description and the appended claims.

BRIEF DESCRIPTION OF DRAWINGS

FIGS. 2A and 2B show a sample collecting device for oilfield applications in an unactuated and an actuated configuration, respectively, in accordance with embodiments disclosed herein.

FIGS. 3A, 3B, 3C, 3D, and 3E show steps of a method of collecting a sample in accordance with embodiments herein.

DETAILED DESCRIPTION

Figure 1:
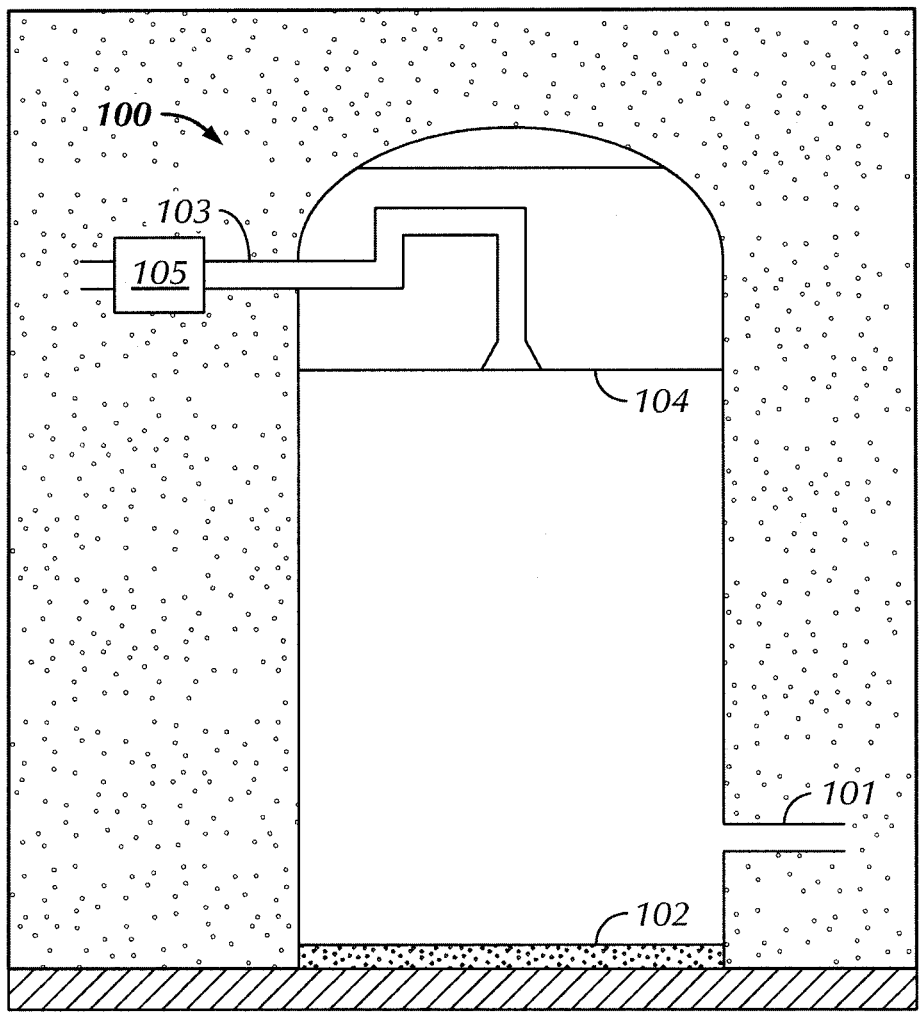
FIG. 1 shows a produced fluid storage container in accordance with embodiments disclosed herein.

Select embodiments of the present disclosure include a sample collecting device having an outer casing, means for actuating the device, means for collecting, storing, and sealing a sample, and means for generating a gas inside the outer casing. The sample collecting device disclosed herein may be used in oilfield applications. However, one of ordinary skill in the art will appreciate that the sample collecting device may be used in other fields, for example, in nuclear applications or in open ocean applications.

Select embodiments of the present disclosure include a sample collecting device and its use in oilfield applications to obtain a sample of sediment from a produced fluid storage container located on a sea floor. In select embodiments, a system is actuated which draws a sample of sediment into a sampler tube of the sample collecting device. Furthermore, select embodiments of the present disclosure include a sample collecting device able to locate, measure, and collect sediment and return to an altitude in the produced fluid storage container without operator input for retrieval.

Advantageously, embodiments disclosed herein provide a sampling device capable of passing through sharp bends in piping or other close fit applications. In one embodiment, a sampling device is provided that is capable of passing through sharp bends in the import and export pipes leading to and from a produced fluid storage container located on a sea floor. Furthermore, embodiments disclosed herein provide a sampling device designed to locate sediment, measure the depth of the sediment, collect a sample, and return to a desired altitude within a container for retrieval without operator input. In select embodiments, the sampling device disclosed herein may be re-set and used to complete multiple dives.

FIG. 2A shows an example of a sample collecting device in accordance with embodiments disclosed herein. As shown, a sample collecting device 200 in accordance with embodiments disclosed herein includes an outer casing 201 with a weighted base 202, a gas zone 203, and at least one vent 204. In one embodiment, outer casing 201 is cylinder-shaped and features a vaulted top as shown. Alternatively, the outer casing may be sphere-shaped or pyramidal (not shown). One of ordinary skill in the art will appreciate that the outer casing may be any shape without departing from the scope of the embodiments disclosed herein. Outer casing 201 may house a hydrostatic pressure measurement device 205, and a valve assembly disposed at least partially within outer casing 201. The valve assembly may include a vacuum reaction chamber 215, and a vacuum reaction chamber valve 216.

In one embodiment, the hydrostatic pressure measurement device 205 may include a capillary tube 217 disposed inside the sample collecting device 200 with an upper sealed end 218 and a one-way valve 219 disposed on a lower end as shown. The capillary tube 217 contains a known volume of air A, which is a compressible fluid, disposed above a column of water W. The hydrostatic pressure acting on one-way valve 219 increases during the descent of sample collecting device 200. Under the increased hydrostatic pressure, the volume of air A is compressed, allowing water to enter into capillary tube 217 through one-way valve 219. The maximum depth reached by sample collecting device 200 is equal to the depth of the sediment surface inside of produced fluid storage container 100. At maximum depth, the air A is under maximum compression for the dive and, correspondingly, the water column W attains its maximum volume. During ascent, one-way valve 219 prevents water W and air A from leaving capillary tube 217, and thus, the contents of capillary tube 217 are kept at a pressure equal to the hydrostatic pressure at the surface of the sediment. The hydrostatic pressure at the surface of the sediment, and a corresponding depth, may be determined based on an analysis of the change in volume of the air A.

In another embodiment, the hydrostatic pressure measurement device 205 may include a calibrated depth gauge (not shown) for collecting depth data that can later be downloaded to a computer and analyzed. In yet another embodiment, the hydrostatic pressure measurement device 205 may include a miniaturized pressure sensor (not shown) for collecting pressure data that can later be downloaded to a computer and analyzed. One of ordinary skill in the art will appreciate that any type of hydrostatic pressure measurement device may be used without departing from the scope of the embodiments disclosed herein. Further, one of ordinary skill in the art will also recognize that additional sensors and data collecting devices may be included in the sample collecting device. For example, the sample collecting device may house a temperature sensor, pH measurement device, resistivity measurement device, and/or a position determination device.

Additionally, the sample collecting device 200 may include a camera (not shown) to capture images or video during the dive. The camera may incorporate a light source such as, for example, light-emitting diode (LED) lights, to improve visibility. In one embodiment, the camera may capture infrared images or video. In some embodiments, the images or video captured by the camera may be saved to a storage device and later downloaded to a computer for analysis. In yet another embodiment, the video or images captured by the video camera may be transmitted in substantially real-time to a remote location for live viewing. An analysis of the video or images captured by the camera may be used to determine more information about the characteristics of the sediment being sampled. For example, the images or video may provide information about the presence of large pieces of sediment that may not be retrievable in the sampler tube. One of ordinary skill in the art will appreciate that other types of cameras, sonar systems, data storage devices, and data transmission methods may be used without departing from the scope of the embodiments disclosed herein.

Vacuum reaction chamber 215 may include a cell 206 capable of maintaining a vacuum under a large hydrostatic head. In one embodiment, cell 206 may be a cylindrical tube or chamber disposed within outer casing 201. One of ordinary skill will appreciate that cell 206 may be formed in any shape, for example, a cylinder, cube, or prism. Additionally, the vacuum reaction chamber 215 includes a one-way valve 207 disposed near an upper end of cell 206 that allows gas to exit cell 206 into outer casing 201 and a septum 209 disposed on the bottom of cell 206. At least one gas generating material 208 may be disposed inside of cell 206. Vacuum reaction chamber 215 may further include a valve 216 disposed at a lower end of the cell 206. Valve 216 may include a needle 210 fluidly connected to a sampler tube 211 having a first end 212 that initially (i.e., when the device is in an unactuated position) protrudes out past base 202 and a diaphragm 213. At least one hole 214 may be disposed on a side of needle 210 proximate an upper end of needle 210.

Referring now to FIGS. 1, 2A, and 3A-E together, sample collecting device 200 fitted with hydrostatic pressure measurement device 205 may enter a produced fluid storage container 100 through an import/export pipe 103 located near an upper end of the storage container 100. A flow of liquid, e.g. water, carries the device 200 through the import/export pipe 103 into the storage container 100. Sample collecting device 200 sinks in water but may have a close-to-neutral buoyancy to aid transportation of sample collecting device 200 into the storage container. For example, in certain embodiments sample control device 200 may have a negative buoyancy of approximately 50 grams. One of ordinary skill in the art will appreciate that sample collecting device 200 may be used in any fluid storage container.

In advance of the deployment of device 200 in import/export pipe 103, water should be circulated into the storage container 100. If possible, hydrocarbon fluids should be circulated out of the storage container 100 prior to the deployment of the device. Once device 200 exits import/export pipe 103 inside the storage container 100, the device sinks through the liquid contained therein, both hydrocarbon fluids and produced water. In one embodiment, sample collecting device 200 may be designed to provide protection from collision between the pipe wall and the sample tube so that accidental actuation may be prevented.

In one embodiment, gas zone 203 is an air pocket. As seen in FIGS. 3A and 3B, the volume of the air pocket decreases due to an increase in hydrostatic pressure during the descent of sample collecting device 200, and additional water enters the outer casing to fill the volume. As the device descends, the hydrostatic pressure acting on the device increases by about 1 atm per 10 meters of increasing depth. The buoyancy and vertical orientation of the device may be maintained by gas zone 203 and weighted base 202. As a result, the rate of descent of the sample collecting device increases as the device descends. One-way valve 207 prevents water from entering rigid cell 206, thereby maintaining a pressure differential between the inside and outside of cell 206, wherein the pressure inside of cell 206 is lower.

In one embodiment, gas zone 203 of device 200 may include an incompressible buoyant material such as, for example, cork or foam, to provide sample collecting device 200 with a pre-determined buoyancy. The incompressible buoyant material may be formed in a hemispherical or toroidal shape (not shown). In one embodiment, a toroidal shaped buoyant material may be included so as to accommodate sampling tubes and other components through the center of the material. One of ordinary skill in the art will appreciate that the incompressible buoyant material may be of any shape or size that provides the sample collecting device with a desired buoyancy.

As the device reaches layer of sediment 102 disposed at the bottom of produced fluid storage container 100, lower end 212 of sampler tube 211 may be pushed up by contact with the sediment layer thus actuating the vacuum reaction chamber valve 216 (FIG. 3C). Lower end 212 may then be level with base 202. The actuated configuration of the sample collecting device is shown in FIG. 2B. During actuation, movement of sampler tube 211 and, thus, needle 210 operably connected to the sampler tube 211, may push the at least one hole 214 disposed on the side of needle 210 through septum 209 and into cell 206. In this actuated configuration, the inside of cell 206 may be fluidly connected with the water contained in needle 210 and in sampler tube 211, and with the sediment contacting end 212 of sampler tube 211. Because the inside and outside of cell 206 are fluidly connected, the pressure differential is released, thereby opening the vacuum contained in cell 206. Water from needle 210 and sampler tube 211 is drawn through hole 214 into cell 206 where it makes contact with at least one gas generating material 208. Sediment 102 is drawn through diaphragm 213 into sampler tube 211.

The gas generating material may be any material that, when dissolved in water, results in a reaction that forms a gas. In one embodiment, the at least one gas generating material 208 comprises a carbonate salt and an organic acid. For example, the reactants may comprise sodium hydrogen carbonate and citric acid. A chemical reaction takes place when water contacts the at least one gas generating material 208, thereby producing a gas. Carbon dioxide gas, sodium citrate, and water form from the reaction of water, sodium hydrogen carbonate, and citric acid. The reaction rate of the gas generating material may be adjusted to suit a specific application. For example, if a fast reaction is required, dehydrated powder forms of the gas generating materials may be used.

In one embodiment, gas generating materials 208 may be formed as two-layer tablets which may be molded by melting gas generating materials 208 separately and pouring them into a mold. The shape and the surface area of the tablets may be designed so as to control the rate of the reaction and gas generation. In one embodiment, gas generation may take place over a period of several minutes, or tens of minutes.

In another embodiment, the gas may be generated by the release of gas from a compressed gas cylinder. A compressed gas cylinder (not shown) may be disposed in the sample collecting device. For example, a compressed gas cylinder such as, a compressed carbon dioxide gas cartridge, may be placed inside sample collecting device 200 proximate sampler tube 211 (i.e., centrally located in the sampling device). In such an embodiment, when sample collecting device 200 is actuated (e.g., when spring 415 and piston assembly 417 are actuated, as discussed below with reference to FIG. 4), the compressed gas cylinder moves upward. A valve (not shown) disposed on an upper end of the compressed gas cylinder (not shown) moves into contact with a corresponding fixed pin member (not shown). Contact between the pin member and the valve releases the gas from the compressed gas cylinder, thereby generating gas that accumulates in gas zone 203. In the embodiment wherein the gas zone 203 includes a buoyant incompressible solid, less gas may be generated in order to obtain a buoyancy sufficient to lift the device off of the sediment surface.

The volume of gas produced increases beyond the volume of cell 206 and creates positive pressure within the cell 206. As shown in FIG. 3D, the produced gas is released through one-way valve 207 into gas zone 203 of outer casing 201. As gas accumulates, water is displaced from outer casing 201 through vents 204. Those of ordinary skill in the art will appreciate that vents 204 may be positioned at any desirable location on outer casing 201. In embodiments having vents 204 located near a top of outer casing 201, less gas will accumulate within sample collecting device 200 than in sample collecting devices 200 having vents 204 disposed near a bottom of outer casing 201. In select embodiments, at least one vent 204 may be disposed on a bottom portion of sample collecting device 200.

The buoyancy of sample collecting device 200 increases due to the accumulation of gas in the gas zone 203. Sample collecting device 200 begins to ascend in the produced fluid storage container 100 in a controlled manner with the collected sediment (FIG. 3E). As sample collecting device 200 rises in produced fluid storage container 100, the hydrostatic pressure decreases and allows the volume of gas in gas zone 203 to expand. Excess gas exits outer casing 201 through the at least one vent 204 disposed in outer casing 201. As discussed above, the location of the at least one vent 204 on outer casing 201 may be important in determining the final buoyancy of the sample collecting device 200. In one embodiment, the buoyancy of sample collecting device 200 is greater than the buoyancy of water and less than the buoyancy of oil such that the sample collecting device 200 ascends in the produced fluid storage container to the interface between the water and oil contained therein. Weighted bottom 202 and gas zone 203 allow the sample collecting device 200 to maintain vertical orientation during ascent, and sampler tube 211 may be fitted with a loose diaphragm 213 to prevent the loss of fine particulate sediments from sampler tube 211. In an alternative embodiment, small weights (not shown) such as, for example, lead pieces, may be distributed within outer casing 201 in such a way that sample collecting device 200 is balanced. For example, small weights may be evenly distributed within outer casing 201 or may be distributed such that more weights are located on one side or location of casing 201 to counteract the weight of other components contained within outer casing 201.

Referring to FIGS. 1 and 2 together, in one embodiment, the level of water-oil interface 104 is located at the same level as the mouth of export pipe 103. Once sample collecting device 200 reaches water-oil interface 104, a catching device 105 disposed in the export line retrieves the device. Fluid may then be pumped through the export pipe 103 to bring sample collecting device 200 to the surface. In one embodiment, the sample collecting device 200 is introduced into and retrieved out of import/export pipe 103 through a pig launcher and a pig receiver, respectively, disposed in import/export pipe 103. Pig launching and receiving technology is well known in the oil field industry and includes a series of valves and angled piping. A mesh arrangement may be included in the pig receiver to allow a flow of fluid through the line, but to trap the sampling device. After retrieval, the device may be cleaned out, reset, and reused.

Figure 4B:
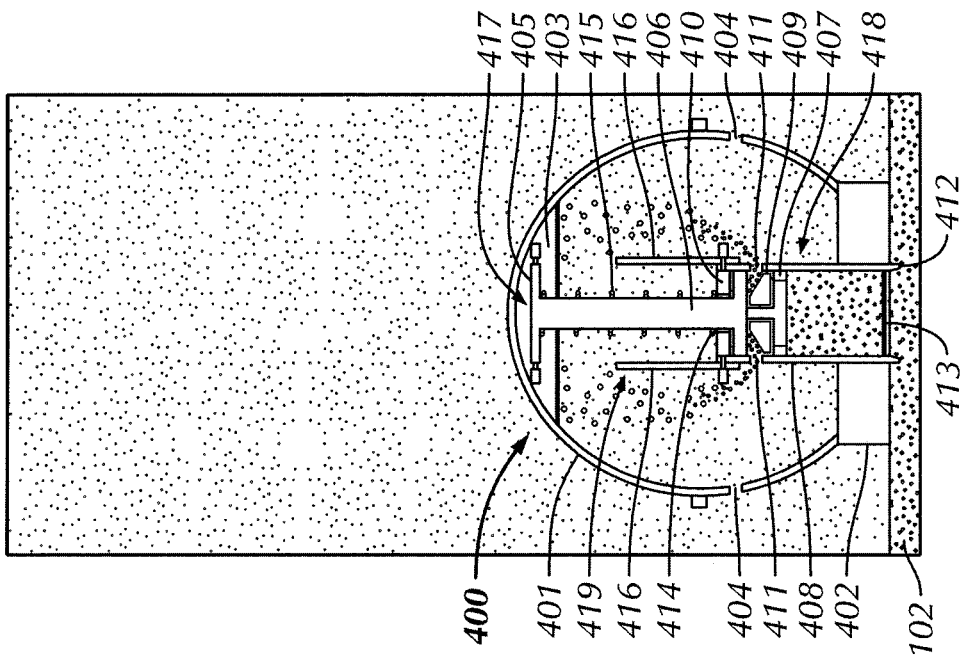
FIGS. 4A and 4B show a sample collecting device for oilfield applications in an unactuated and an actuated configuration, respectively, in accordance with embodiments disclosed herein.
Figure 4A:
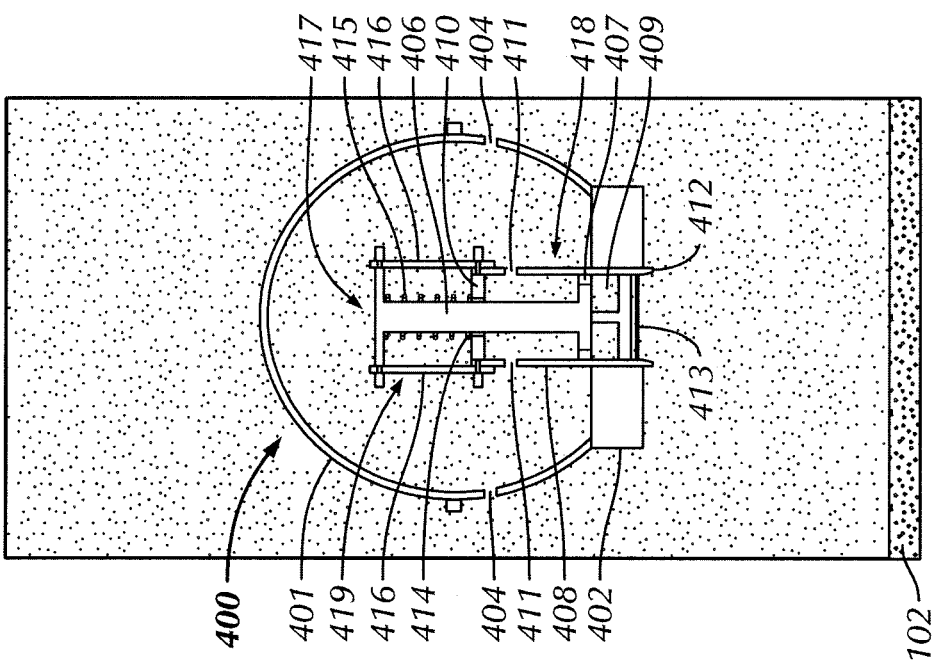

FIG. 4A shows another example of a sample collecting device according with embodiments disclosed herein. A sample collecting device 400 in accordance with embodiments disclosed herein includes an outer casing 401 with a weighted base 402, a gas zone 403 (FIG. 4B), and at least one vent 404. A valve assembly configured to obtain a sample of a sample material may be disposed at least partially within outer casing 401. In one embodiment, outer casing 401 is sphere-shaped as shown, and may be formed from two halves fastened together along a horizontal join. In alternative embodiments, the outer casing may be cylinder-shaped or pyramidal (not shown). One of ordinary skill in the art will appreciate that the outer casing may be any shape without departing from the scope of embodiments disclosed herein.

Figure 5A:
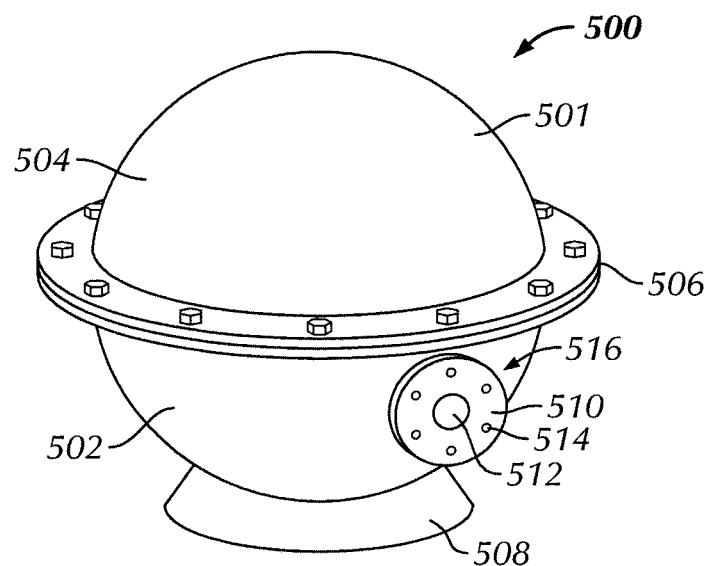
FIGS. 5A and 5B show a perspective view and a cross-sectional view, respectively, of a sample collecting device for oilfield applications in accordance with embodiments disclosed herein.
Figure 5B:
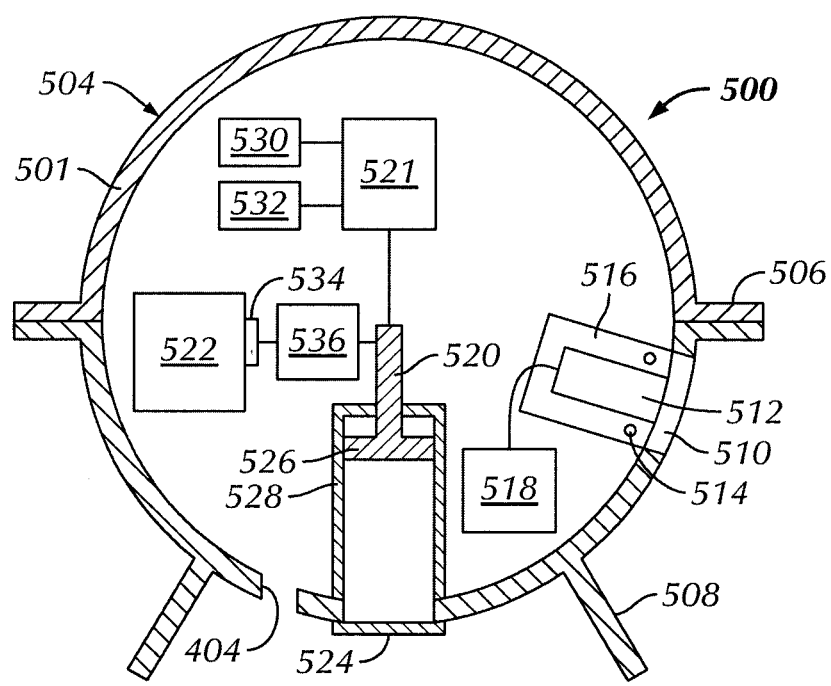

Referring briefly to FIGS. 5A and 5B, an example of a sample collecting device 500 having a sphere-shaped outer casing 501 is shown. Sample collecting device 500 is shown having a lower half 502 and an upper half 504 of an outer casing 501 fastened at a horizontal join 506. In certain embodiments, sphere-shaped outer casing 501 may measure between approximately 5 inches and 6 inches in diameter; however, those having ordinary skill in the art will appreciate that larger and smaller diameters may also be used. Outer casing 501 may be formed from a metal material such as, for example, steel. The two halves of outer casing 501 may be fastened together using any fastening means known in the art such as, for example, bolts, screws, welds, and adhesives. Lower half 502 of outer casing 501 may include an annular skirt 508 configured to contact sediment 102 (FIG. 1) in produced fluid storage container 100 (FIG. 1) and to properly land sample collecting device 500 on sediment 102 in a vertical position.

Referring back to FIGS. 4A and 4B, outer casing 401 may house a hydrostatic pressure measurement device (not shown), a piston assembly 417, a cylinder arrangement 418, and an actuation system 419. In one embodiment, the hydrostatic pressure measurement device (not shown) may include a calibrated capillary tube disposed inside of the sample collecting device 400 with an upper sealed end and a one-way valve disposed on a lower end. The capillary tube contains a known volume of gas disposed above a column of water, wherein the gas has limited water solubility. In one embodiment, the gas used is air. The hydrostatic pressure acting on the one-way valve increases during the descent of sample collecting device 400. Under the increased hydrostatic pressure, the volume of air is compressed, allowing water to enter into the capillary tube through the one-way valve. The maximum depth reached by sample collecting device 400 is equal to the depth of the sediment surface inside of produced fluid storage container 100. At maximum depth, the air is under maximum compression for the dive and, correspondingly, the water column attains its maximum volume. During ascent, the one-way valve prevents water and air from leaving the capillary tube and, thus, the contents of the capillary tube are kept at a pressure equal the hydrostatic pressure at the surface of the sediment. The hydrostatic pressure at the surface of the sediment, and a corresponding depth, may be determined based on an analysis of the change in volume of the air A.

In one embodiment, the hydrostatic pressure measurement device may include a calibrated depth gauge for collecting depth data that may later be downloaded to a computer for analysis. In another embodiment, the hydrostatic pressure measurement device may include a miniaturized pressure sensor for collecting pressure data that may later be downloaded to a computer for analysis. For example, a pressure monitoring cell, commercially available from Lotek Wireless (Ontario, Canada), may be disposed within sample collecting device 400. In yet another embodiment, the hydrostatic pressure measurement device may transmit depth data to a remote data receiver in substantially real-time. One of ordinary skill in the art will appreciate that any type of hydrostatic pressure measurement device may be used without departing from the scope of the embodiments disclosed herein. One of ordinary skill in the art will also recognize that additional sensors and data collecting devices may be included in the sample collecting device. For example, the sample collecting device may house a temperature sensor, pH measurement device, resistivity measurement device, and a position determination device. Additionally, the sample collecting device may include a camera to capture images or video during the dive, as discussed above.

Referring briefly to FIGS. 5A and 5B, outer casing 501 may include a transparent window 510 disposed therein. In certain embodiments, window 510 may be formed from a transparent thermoplastic material such as, for example, polymethyl methacrylate. A video camera 512 and lights 514 such as, for example, LED lights, may be disposed in a water-tight chamber 516 positioned adjacent the transparent window. Video camera 512 may be configured to record video onto a built-in storage chip that may later be retrieved and connected to a computer using, for example, a USB connection. Alternatively, video camera 512 may wirelessly transmit video feed to a display unit. Video camera 512 and lights 514 may be powered by a battery 518 such as, for example, a 9-volt battery, having an on/off switch (not shown) positioned on an outside surface of outer casing 401.

Referring back to FIGS. 4A and 4B, sample collecting device 400 may include a valve assembly having a sampler tube 408, a platform 405 disposed at an upper end of sampler tube 408, a biasing member disposed between the platform and the upper end of the sampler tube, and at least one biasing member restraining link disposed between platform 405 and the upper end of sampler tube 408. Piston assembly 417 includes a central rod 406, at least one sealing element 407 that creates a seal with sampler tube 408, and at least one gas generating material 409. Central rod 406 may be integrally formed with or otherwise coupled to platform 405 such that there is no relative movement between central rod 406 and platform 405. Sealing elements 407 are disposed around gas generating material 409 and sealingly engage sampler tube 408 such that water contact with gas generating material 409 is prevented until the piston is actuated.

Cylinder arrangement 418 may guide the movement of piston arrangement 417 and may include sampler tube 408, wherein windows 411 may be disposed on sampler tube 408. A lower end 412 of sampler tube 408 may be fitted with a diaphragm 413. A hole 414 may be disposed in upper end 410 of sampler tube 408 such that central rod 406 extends therethrough.

A valve assembly may include actuation system 419 including a biasing member such as, for example, spring 415, disposed around central rod 406, wherein spring 415 is configured to be held in an energy storing position by at least one restraining link 416 (FIG. 4A). In one embodiment, spring 415 is a compression spring held in a compressed position by restraining links 416 as shown in FIG. 4A. In an alternate embodiment, those of ordinary skill in the art will appreciate that the described device may be reconfigured to include an extension spring rather than a compression spring. In alternative embodiments, a restraining pin (not shown) may be used to maintain a compressive force on spring 415.

Referring to FIGS. 1 and 4A together, sample collecting device 400 enters a produced fluid storage container 100 through an import/export pipe 103. Sample collecting device 400 sinks in water but has close-to-neutral buoyancy to aid transportation of the device 400 into the storage container. The buoyancy of sample collecting device 400 may be adjusted by using buoyancy adjusting objects, the buoyancy adjusting objects having a known buoyancy. In certain embodiments, the objects may be capable of withstanding a hydrostatic pressure at the depth of sediment 102. For example, rigid plastic balls (not shown) having a diameter between approximately 0.5 inches and approximately 1 inch may be used. In certain embodiments, the plastic balls may be hollow, or may be filled with a gas or other buoyant material. The plastic balls may be provided to give sample collecting device 400 a negative initial buoyancy in water of between approximately 25 grams and approximately 75 grams. It may be desirable to adjust the buoyancy of sample collecting device 400 so that sample collecting device 400 is not too heavy to flow through import/export pipe 103 having bends and vertical sections.

Sample collecting device 400 may include a gas zone 403 such as an air pocket, which may be adjusted to provide a desired buoyancy. The volume of the air pocket decreases as sample collecting device 400 sinks and additional water enters the outer casing 401 through vents 404. As a result, the rate of descent of the sample collecting device 400 increases and the device lands on a layer of sediment 102 disposed on the bottom of produced fluid storage container 100. In some embodiments, the gas zone of the device may include an incompressible buoyant material, as described above.

Additionally, to maintain sample collecting device 400 in an upright position during transportation to container 100, weighted materials may be selectively placed near a base of sample collecting device 400. In certain embodiments, small pieces of lead may be fitted into sample collecting device 400 for balancing so that sample collecting device 400 may be oriented with the base downward and horizontal.

The at least one restraining link 416 may be made of a material that degrades over time when exposed to water. In one embodiment, the at least one restraining link 416 is made of cardboard chemically treated to degrade over a desired amount of time. In another embodiment, the at least one restraining link 416 is made of medium density fiberboard (MDF). Alternatively, restraining link 416 may be formed from a water degradable plastic material, such as polyvinyl alcohol. One of ordinary skill in the art will appreciate that other materials may be used for the restraining link 416 such that the material degrades or breaks at a predetermined time or condition, thereby releasing the piston assembly 417.

The geometry, material, and dimensions of the at least one restraining link 416 may be varied to control the amount of time required in contact with water before structural failure of the at least one link 416 occurs. For example, the width of the at least one restraining link 416 may be increased or decreased, resulting in a longer or a shorter time until failure, respectively. Additionally, the at least one restraining link 416 may be formed with a varying width or diameter along its length (e.g., a notch may be formed in the restraining link 416) such that a weak point is formed which may lead to more rapid degradation and structural failure at that point. In certain embodiments, restraining link 416 may be designed to undergo structural failure after between approximately 3 hours and approximately 5 hours of submersion.

Additionally, although restraining links 416 are shown, those of ordinary skill in the art will appreciate that a pin (not shown) formed from a material degradable in water may alternatively be used to maintain compression of spring 415. For example, a water soluble plastic pin may be used. A pin in accordance with the present disclosure may be less than approximately 0.5 inches in length and may have a square cross section having a width and height measuring between approximately 0.05 inches and 0.1 inches. Those of ordinary skill in the art will appreciate that a pin having any other desired cross-sectional size or shape such as, for example, circular, triangular, or oval, may be used.

After significant degradation takes place, structural failure of the at least one restraining link 416 may occur as shown in FIG. 4B, thereby actuating piston assembly 417 by releasing the load imposed on spring 415 and allowing spring 415 to return to its unloaded position. Platform 405 and, hence, the entire piston assembly 417, may be pushed upward by the released spring 415. Suction created by the drawing up of the piston assembly pulls sediment 102 into sampler tube 408. A one-way valve 524 (FIG. 5B) may be disposed on a bottom opening of sampler tube 408 such that sediment 102 may enter sampler tube 408 but may be stopped from falling out of sampler tube 408. In certain embodiments, one-way valve 524 may be disc-shaped, having a support frame and a flexible membrane to allow flow of sediment 102 into sampler tube 408 and to prevent sediment 102 from exiting sampler tube 408.

Actuation of the piston assembly may actuate a buoyancy generating device configured to increase the buoyancy of sample collecting device 400. In certain embodiments, the buoyancy generating device may include a gas generating material or a compressed gas cartridge. Actuating of the piston assembly may move gas generating material 409 into alignment with sampler tube windows 411, allowing water to make contact with gas generating material 409. Gas generating material 409 may be any material that, when dissolved in water, results in a reaction that forms a gas. In one embodiment, the at least one gas generating material comprises a carbonate salt and an organic acid. For example, the reactants may comprise sodium hydrogen carbonate and citric acid. A chemical reaction takes place when water contacts the at least one gas generating material, thereby producing a gas. Carbon dioxide gas, sodium citrate, and water form from the reaction of water, sodium hydrogen carbonate, and citric acid. The reaction rate of the gas generating material may be adjusted to suit a specific application. For example, if a fast reaction is required, dehydrated powder forms of the gas generating materials may be used.

In one embodiment, the gas generating materials may be formed as two-layer tablets which may be molded by melting the gas generating materials separately and pouring them into a mold. The shape and the surface area of the tablets may be designed so as to control the rate of the reaction and gas generation. In one embodiment, gas generation may take place over a period of several minutes, or tens of minutes. In another embodiment, the gas may be generated by the release of a compressed gas cylinder, as discussed above.

Referring briefly to FIGS. 5A and 5B, in an alternative embodiment, a plunger rod 520 and a carbon dioxide gas cartridge 522 having a sealed opening 534 may be provided within sample collecting device 500. Upward movement of plunger rod 520 may cause a lever (not shown) to move, the lever configured to actuate piercing mechanism 536. Alternatively, plunger rod 520 may be configured to pierce sealed opening 524 by moving upward and into contact with sealed opening 524 of carbon dioxide gas cartridge 522 after a sample of sediment 102 (FIG. 1) is obtained, thereby releasing compressed carbon dioxide gas into sample collecting device 500. Piercing mechanism 536 may include a needle configured to enter carbon dioxide gas cartridge 522 breaking the seal of carbon dioxide gas cartridge 522 through sealed opening 524 and allowing compressed carbon dioxide gas to escape into outer casing 501.

Carbon dioxide gas cartridge 522 may be a 12 gram cartridge capable of releasing between approximately 12 liters of gas at ambient pressure. Under a hydrostatic pressure of approximately 10 bar, the 12 gram carbon dioxide gas cartridge may release approximately 1.2 liters of gas. Those of ordinary skill in the art will appreciate that other sizes of cartridges 522 may be used to provide more or less gas. In select embodiments, the amount of gas required to lift sample collecting device 500 is approximately 500 cubic centimeters. As sample collecting device 500 rises and hydrostatic pressure acting on sample collecting device 500 decreases, the released gas may expand and exit outer casing 501 through vents 404 disposed in a bottom portion of sample collecting device 500.

Referring again to FIGS. 4A and 4B, a volume of gas may accumulate in gas zone 403 and may displace a volume of water through the at least one vent 404. The buoyancy of sample collecting device 400 increases due to the accumulation of gas in the gas zone and begins to ascend in the produced fluid storage container 100. Excess gas exits the outer casing 401 through the at least one vent 404 disposed in outer casing 401. The location of the at least one vent 404 on outer casing 401 may be important in determining the final buoyancy of the sample collecting device 400. In one embodiment, the buoyancy of sample collecting device 400 is greater than the buoyancy of water and less than the buoyancy of oil such that the sample collecting device 400 ascends in the produced fluid storage container to the interface between the water and oil contained therein. Weighted bottom 402 and gas zone 403 may allow the sample collecting device 400 to maintain vertical orientation during ascent. Alternatively, as discussed above, an annular skirt 508 (FIGS. 5A and 5B) may be attached to, or integrally formed with, lower portion 502 of outer casing 501, and balancing weights (not shown) may be disposed therein to provide balance and orientation. Sampler tube 408 may be fitted with a loose diaphragm 413 to prevent the loss of fine particulate sediments from the sampler tube 408 during retrieval.

In one embodiment, the level of water-oil interface 104 is located at the same level as the mouth of import/export pipe 103. Once sample collecting device 400 reaches water-oil interface 104, a catching device 105 disposed in import/export line 103 retrieves the device. Fluid may then be pumped through import/export pipe 103 to bring sample collecting device 400 to the surface. In one embodiment, the sample collecting device 200 is introduced into and retrieved out of import/export pipe 103 through a pig launcher and a pig receiver, respectively, disposed in the import/export pipe 103. Pig launching and receiving technology is well known in the oil field industry and includes a series of valves and angled piping. A mesh arrangement may be included in the pig receiver to allow a flow of fluid through the line, but trap the sampling device.

After use, the sample collecting device may be emptied of its collected sample and cleaned. The sample may be analyzed and data from the various sensors may be downloaded to a computer and analyzed. The sample collecting device may be re-set in preparation for another run or dive. For example, spring 415 may be restored to an energy storing position and a new set of spring restraining links 416 may be attached to hold the spring. Sample collecting device 400 may then be used on another dive to collect another sample.

Although mechanical systems for actuating a sample collecting device are discussed, automated systems may also be used. Referring to FIGS. 5A and 5B, a sample collecting device 500 may include a programmable logic controller ("PLC") 521 configured to actuate plunger 526, thereby drawing a sample of sediment into sampler tube 528. A pressure sensor 530 and/or a timer 532 may be operatively coupled to PLC 521. In such an embodiment, PLC 521 may actuate plunger 526 at a predetermined depth as sensed by pressure sensor 530. In certain embodiments, sample collecting device 500 may be equipped with a contact sensor (not shown) configured to detect a contact pressure between annular skirt 508 and sediment. The contact sensor may be operatively coupled to PLC 521 such that when a contact pressure is detected, PLC 521 instructs actuation of plunger 526. Alternatively, PLC 521 may actuate plunger 526 after a predetermined amount of time has elapsed, as measured by timer 532. Those of ordinary skill in the art will appreciate that PLC 521 may be remotely actuated by an operator at a desired time based on live video feed sent from camera 512 to a remove display unit. In addition to controlling the intake of a sample of sediment into sampler tube 528, PLC 521 may further control the release of gas from a compressed gas cartridge to lift sample collecting device 500 off of a sediment layer.

Embodiments disclosed herein advantageously provide a sampling device capable of being deployed through piping. Further, a sampling device in accordance with embodiments disclosed herein provides sampling of sediment and/or liquid samples. Additionally, a sampling device in accordance with embodiments disclosed herein may provide information regarding hydrostatic pressure, depth, temperature, pH, and/or resistivity. Furthermore, a sampling device in accordance with embodiments disclosed herein may provide video and/or images that may be analyzed to provide information regarding the sample material.

As mentioned above, while embodiments discussed above relate to oil and gas applications, the present invention is not so limited in its field of use, and those having ordinary skill in the art will appreciate that a sampling device may be useful in any field requiring sampling of sediments, and the like.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed:

1. A sample collecting device comprising:
   an outer casing having a base;
   a valve assembly disposed at least partially within the outer casing, the valve assembly comprising a sampler tube configured to draw a sample of a sample material up through an opening in the base of the outer casing to isolate the sample within the sampler tube; and
   a buoyancy generating device configured to selectively increase buoyancy of the sample collecting device.

2. The sample collecting device of claim 1, further comprising:
   a pressure sensor wherein the pressure sensor detects pressure data.

3. The sample collecting device of claim 1, wherein the valve assembly further comprises:
   a platform disposed at an upper end of the sampler tube;
   a biasing member disposed between the platform and the upper end of the sampler tube; and
   at least one biasing member restraining link coupled to the platform and the upper end of the sampler tube.

4. The sample collecting device of claim 1, wherein the buoyancy generating device comprises at least one of a compressed gas cartridge and a gas generating material.

5. The sample collecting device of claim 3, wherein the at least one biasing member restraining link comprises a material that deteriorates in water.

6. The sample collecting device of claim 1, further comprising a programmable logic controller operatively coupled to at least one selected from a group consisting of a pressure sensor and a timer.

7. The sample collecting device of claim 6, wherein the programmable logic controller controls at least one selected from a group consisting of actuation of a sampler tube plunger at a predetermined depth sensed by the pressure sensor, actuation of the sampler tube plunger after a predetermined time measured by the timer, and actuation of a buoyancy generation device.

8. The sample collecting device of claim 1, further comprising:
   an annular skirt disposed on a lower portion of the outer casing; and
   at least one vent disposed on the lower portion of the outer casing.

9. The sample collecting device of claim 1, further comprising:
   a transparent window disposed in the outer casing;
   a camera disposed within the outer casing adjacent the transparent window, wherein a lens of the camera is oriented toward the transparent window; and
   a plurality of lights disposed around the lens of the camera.

10. The sample collecting device of claim 9, wherein the plurality of lights are light-emitting diode lights.

11. The sample collecting device of claim 1, further comprising a plurality of buoyancy adjusting objects configured to provide the sample collecting device with a predetermined initial buoyancy.

12. A method comprising:
    entering a sample collecting device into a fluid storage container having a sample material disposed therein, wherein the sample collecting device includes at least an outer casing and a valve assembly having a sampler tube, wherein the valve assembly is disposed at least partially within the outer casing;
    contacting a surface of the sample material with a lower end of the outer casing;
    obtaining a sample of the sample material by drawing a sample into the sampler tube of the sample collecting device through an opening in the lower end of the outer casing; and
    removing the sample collecting device from the fluid storage container.

13. The method of claim 12, wherein the fluid storage container is disposed on a sea floor.

14. The method of claim 12, further comprising:
    determining an amount of the sample material present in the fluid storage container.

15. The method of claim 14, wherein the determining the amount of the sample material present in the fluid storage container comprises:
    measuring hydrostatic pressure at the surface of the sample material.

16. The method of claim 12, wherein obtaining the sample comprises actuating the valve assembly by at least one selected from a group consisting of structural failure of a restraining pin and actuation instruction from a programmable logic controller, wherein the actuating the valve assembly creates a suction and draws the sample material into the sampler tube.

17. The method of claim 12, wherein removing the sample collecting device from the fluid storage container further comprises:
    increasing a buoyancy of the sample collecting device; and
    ascending the sample collecting device to a desired area of the fluid storage container for retrieval.

18. The method of claim 17, wherein increasing the buoyancy of the sample collecting device comprises at least one selected from a group consisting of reacting at least one gas generating material with water to form a gas, and releasing a compressed gas from a compressed gas cartridge.

19. The method of claim 17, wherein the increasing the buoyancy of the sample collecting device is actuated by a programmable logic controller.

20. A sample collecting device comprising:
    an outer casing having a base;
    a valve assembly disposed at least partially within the outer casing, the valve assembly comprising a sampler tube configured to draw a sample of a sample material up through an opening in the base of the outer casing to isolate the sample within the sampler tube;
    an annular skirt disposed on a lower portion of the outer casing; and
    at least one vent disposed on the lower portion of the outer casing.

21. The sample collecting device of claim 20 further comprising a buoyancy generating device configured to selectively increase buoyancy of the sample collecting device.

* * * * *